US009759655B2

(12) United States Patent
Koulikov (10) Patent No.: US 9,759,655 B2
(45) Date of Patent: Sep. 12, 2017

(54) LASER BEAM STOP ELEMENTS AND SPECTROSCOPY SYSTEMS INCLUDING THE SAME

(71) Applicant: LI-COR, Inc., Lincoln, NE (US)

(72) Inventor: Serguei Koulikov, Los Altos, CA (US)

(73) Assignee: Li-Cor, Inc., Lincoln, NE (US)

( * ) Notice: Subject to any disclaimer, the term of this patent is extended or adjusted under 35 U.S.C. 154(b) by 127 days.

(21) Appl. No.: 14/870,425

(22) Filed: Sep. 30, 2015

(65) Prior Publication Data

US 2016/0091420 A1 Mar. 31, 2016

Related U.S. Application Data

(60) Provisional application No. 62/057,499, filed on Sep. 30, 2014.

(51) Int. Cl.
| | |
|---|---|
| *G01J 4/04* | (2006.01) |
| *G01N 21/39* | (2006.01) |
| *H01S 5/00* | (2006.01) |
| *H01S 3/081* | (2006.01) |
| *G02B 5/30* | (2006.01) |
| *G02B 5/20* | (2006.01) |
| *G01N 21/17* | (2006.01) |

(52) U.S. Cl.
CPC ............ *G01N 21/39* (2013.01); *G02B 5/205* (2013.01); *G02B 5/3066* (2013.01); *H01S 3/081* (2013.01); *H01S 5/0014* (2013.01); *H01S 5/0078* (2013.01); *G01N 2021/1704* (2013.01); *G01N 2021/399* (2013.01); *G01N 2201/0642* (2013.01)

(58) Field of Classification Search
CPC ..................................... G01J 4/00; G01J 4/04
USPC ......................................................... 356/369
See application file for complete search history.

(56) References Cited

U.S. PATENT DOCUMENTS

| | | | | | |
|---|---|---|---|---|---|
| 4,960,310 | A | * | 10/1990 | Cushing | G02B 5/28 359/360 |
| 5,091,244 | A | * | 2/1992 | Biornard | C03C 17/3435 204/192.26 |
| 5,521,759 | A | * | 5/1996 | Dobrowolski | G02B 1/116 348/834 |
| 5,973,864 | A | * | 10/1999 | Lehmann | G01J 3/42 356/300 |

(Continued)

FOREIGN PATENT DOCUMENTS

| | | |
|---|---|---|
| GB | 789597 A | 1/1958 |
| GB | 1025185 A | 11/1963 |

OTHER PUBLICATIONS

International Search Report and Written Opinion for PCT/US15/53219 dated Dec. 28, 2015.

*Primary Examiner* — Roy M Punnoose
(74) *Attorney, Agent, or Firm* — Leydig, Voit & Mayer, Ltd.; Gerald T. Gray (57) ABSTRACT

Laser-based spectroscopy systems and methods including a laser source that emits a beam of radiation, an optical resonant cavity having at least two cavity mirrors, and at least one beam filtering element positioned along a path of the beam external to the cavity and having a front surface, wherein the front surface is oriented such that an intersection of the beam and the surface is at an angle, such as the Brewster's angle or a pseudo-Brewster's, that reduces or eliminates reflection of a predominant polarization component of the beam by the filtering element.

18 Claims, 6 Drawing Sheets

20 – V-shaped resonant cavity
12 – laser
13 – mode-matching optics
14 – folding mirror
15 – detector
16 – beam stop element (e.g., neutral density filter)

(56) References Cited

U.S. PATENT DOCUMENTS

| | | |
|---|---|---|
| 6,611,546 B1 | 8/2003 | Garnache et al. |
| 7,342,661 B2 | 3/2008 | Ebert et al. |
| 8,040,509 B2 | 10/2011 | Larsen et al. |
| 2004/0027652 A1* | 2/2004 | Erdogan ................ G02B 5/285 359/359 |
| 2014/0029108 A1* | 1/2014 | Bockmeyer ............ G02B 5/205 359/642 |
| 2014/0192347 A1 | 7/2014 | Koulikov et al. |

* cited by examiner

20 – V-shaped resonant cavity
12 – laser
13 – mode-matching optics
14 – folding mirror
15 – detector
16 – beam stop element (e.g., neutral density filter)

Figure 4

120 – ring resonant cavity
112 – laser
113 – mode-matching optics
114 – mirror
115 – detector
116 – beam stop element

LASER BEAM STOP ELEMENTS AND SPECTROSCOPY SYSTEMS INCLUDING THE SAME

CROSS-REFERENCE TO RELATED APPLICATIONS

This patent application claims the benefit of U.S. Provisional Patent Application No. 62/057,499, filed Sep. 30, 2014, which is incorporated herein by reference.

BACKGROUND

The present disclosure relates to spectral measurement systems and devices and more particularly to apparatus for measuring spectral content with light reflection and scattering reduction features. Such spectral content measurements can be used for qualitative and quantitative trace gas detection.

In spectral measurement systems, such as in optical spectroscopy measurement systems, stray light at various frequencies may cause unwanted results and possible reduce the accuracy of measurements. Such stray light, often in the form of reflected or scattered excitation light or reflected or scattered emission light, can be deleterious to optical spectroscopy measurements. Accordingly, it is desirable to provide systems and methods for reducing or eliminating stray light in spectral measurement systems.

SUMMARY

The present disclosure relates to spectral measurement systems, methods and devices and more particularly to systems and methods for measuring spectral content with light reflection and scattering reduction features. Embodiments advantageously provide for a reduction in the amount of reflected and scattered incident light present in the system and thereby enhance spectral content measurements, such as laser spectroscopy based gas absorption measurements.

In certain embodiments, an apparatus includes a laser source, or other source that emits directed illumination (e.g., a beam of radiation) and one or more elements to absorb the emitted light beam with a minimum amount of reflected and scattered radiation. In one embodiment, the apparatus has at least one filtering element such as a light absorptive element, or a non-absorptive element, which is placed at an angle relative to the incident light. For example, a surface of the filtering element is arranged such that an intersection of an incident beam and the surface is at an angle that reduces reflection of the beam by the surface. Additional filter elements can be placed in series in such configuration, where a reflected light from one element is incident on the next element at the above-mentioned angle. The angle is chosen to reduce or minimize an intensity of the reflected beam. One example of an angle is the Brewster angle.

According to an embodiment, a laser-based spectroscopy system is provided that typically includes a laser source that emits a beam of radiation, an optical resonant cavity having at least two cavity mirrors, and at least one beam filtering element positioned along a path of the beam external to the cavity and having a front surface, wherein the front surface is oriented such that an intersection of the beam and the surface is at an angle that reduces or eliminates reflection of a predominant polarization component of the beam by the filtering element.. The path of the beam external to the cavity may include reflections off of optical elements such as cavity mirrors and it may include light escaping from a cavity mirror.

In certain aspects, the light laser source is a diode laser source. In certain aspects, the at least one beam filtering element comprises an absorptive glass material and the angle is at a pseudo-Brewster angle. In certain aspects, the angle is at a Brewster angle. In certain aspects, the at least one beam filtering element is positioned to receive light reflected off of one of said cavity mirrors. In certain aspects, the at least one beam filtering element is positioned to receive light emerging from one of said cavity mirrors. In certain aspects, the at least one beam filtering element includes a neutral density filter. In certain aspects, the system includes at least two beam filtering elements, each positioned along a path of the beam and having a front surface, wherein each said front surface is oriented such that an intersection of the beam and said front surface is at an angle that reduces reflection of a predominant polarization component of the beam by said surface. In certain aspects, the system includes a second beam filtering element positioned to interact with light reflected from the at least one beam filtering element.

According to another embodiment, an apparatus for detecting one or more analyte species present in a gaseous or liquid medium is provided. The apparatus typically includes a resonant optical cavity having at least two cavity mirrors, one of which is a cavity coupling mirror, a laser that emits a beam of laser light, mode matching optics configured to couple the beam of laser light to the cavity via the cavity coupling mirror, and a detector configured to measure an intensity of intracavity optical power of light circulating in the cavity and to generate a signal representing the intracavity optical power of light circulating in the cavity. The apparatus also typically includes a first beam stop element positioned external to the resonant optical cavity and arranged such that an intersection of the beam and a front surface of the first beam stop element is at an angle that reduces or eliminates reflection of a predominant polarization component of the beam by the first beam stop element. The path of the beam external to the cavity may include reflections off of optical elements such as cavity mirrors and it may include light escaping from a cavity mirror.

In certain aspects, the laser is a diode laser. In certain aspects, the first beam stop element includes an absorptive glass material, and the angle is at a pseudo-Brewster angle. In certain aspects, the angle is at a Brewster angle. In certain aspects, the first beam stop element is positioned to receive light reflected off of one of said at least two cavity mirrors. In certain aspects, the first beam stop element is positioned to receive light emerging from one of said at least two cavity mirrors. In certain aspects, the first beam stop element includes a neutral density filter. In certain aspects, the apparatus further includes a second beam stop element positioned to interact with light reflected from the first beam stop element.

According to yet another embodiment, an optical spectroscopy apparatus is provided that typically includes a light source that emits a beam of radiation, and at least one beam filtering element positioned along a path of the beam and having a surface, wherein the surface is oriented such that an intersection of the beam and the surface is at an angle that reduces or eliminates reflection of a predominant polarization component of the beam by the at least one beam filtering element. In certain aspects, the at least one beam filtering element comprises an absorptive glass material, and wherein the angle is at a pseudo-Brewster angle. In certain aspects, the light source includes a laser source.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

The present disclosure relates generally to trace gas detection and more specifically to systems and methods for detecting trace gasses with light reflection and scattering reduction features.

Figure 1:
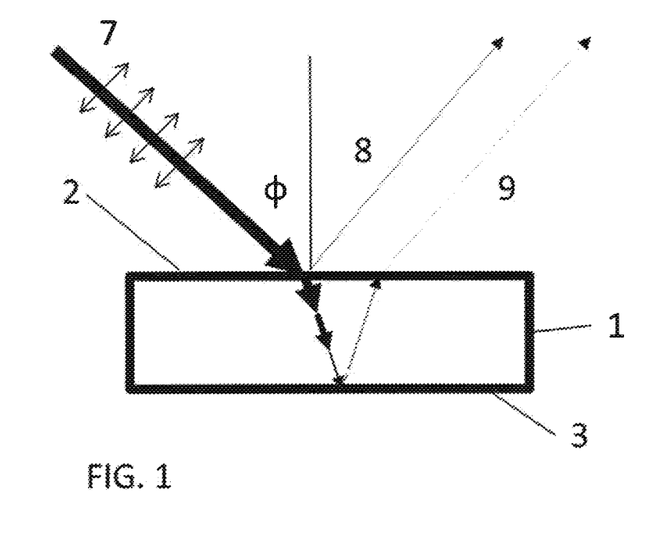
FIG. 1 shows an example of a neutral density filter as a beam stop or filter element according to an embodiment.

FIG. 1 shows an example of a beam stop or filter element 1 according to an embodiment. The terms "beam stop element," "beam filtering element," "filter element," and the like will be used interchageably herein. In certain embodiments, a beam stop element includes a neutral density filter. As shown, a p-polarized laser beam 7 (p-polarization represented as parallel to page of FIG. 1, whereas s-polarization is represented as normal to, or coming out of, the page of FIG. 1) is incident on the front surface 2 of the filter element 1 at an angle $\phi$, at which a reflected beam 8 has a minimum intensity. For a non-absorptive material, the desired angle $\phi$ is the Brewster's angle, which is an angle of incidence at which light with a particular polarization is perfectly transmitted through a transparent dielectric surface, with no reflection.

However, for absorptive materials, a pseudo-Brewster angle may be used. The pseudo-Brewster angle is defined as the angle where the reflection for a p-polarized beam is minimal, i.e., the beam penetration in the material is maximal. When a medium has an optical loss, the index of refraction n becomes complex: $n=n'+ik$, where $k=\alpha\lambda/(4\pi)$, $\alpha$ is the absorption coefficient, and $\lambda$ is wavelength. Ionicaly colored glass KG5 from Schott [http://www.schott.com/advanced_optics/english/download/schott-shortpass-kg5-dec-2014-en.pdf] is an example of the absorbing media used to make NIR absorptive ND filters (e.g., Thorlabs, P/N NENIR560B). KG5 glass has k value around 0.001 in the NIR spectral region. FIG. 2 in the Chapter 5 [http://photonics.intec.ugent.be/education/IVPV/res_handbook/v1ch05.pdf] from Handbook of Optics, $2^{nd}$ Edition, McGRAW-HILL, INC, illustrates how the reflection from a media depends on the real and imaginary parts of the refractive index. Other angles where the reflection is reduced are also useful. If partially polarized or unpolarized light is irradiated on the front surface 2, the absorptive element can be placed at an angle to minimize the total reflection or the reflection for the p-polarized component. In the latter case, the reflected light 8 will have a predominant polarization (s-polarization) component. Another (second) absorptive element can be used to completely or partially absorb the reflected light 8 reflected from the first element, e.g., minimize reflection of the s-polarization component in the reflected light 8 incident on the second element.

The front surface 2 of the absorptive element can be optically polished to minimize the scattering light. The second surface 3 of the absorptive element can be also optically polished and/or may include a reflective coating thereon (e.g., gold coating or dielectric coating). The reflective coating might completely stop penetration of the light further, and reflect back some light, which passes through the absorptive element, as light beam 9 as shown in FIG. 1.

Figure 2:
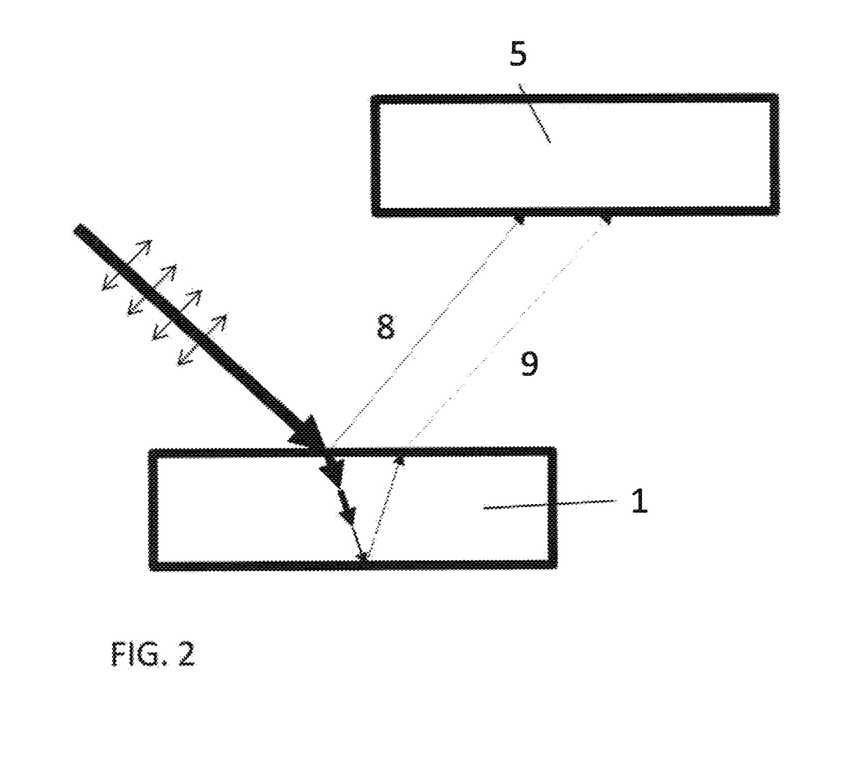
FIG. 2 shows a configuration with two beam stop elements according to another embodiment.

FIG. 2 illustrates a configuration with two beam stop elements, e.g., beam stop element 1 and second beam stop element 5. Each beam stop element may include a neutral density filter. As shown, the beam stop elements 1, 5 are positioned and arranged such that the incident linearly p-polarized light beam 7 hits the first element 1 at the pseudo-Brewster angle, and the reflected beam 8, reflected from first element 1, also hits the second element 5 at the pseudo-Brewster angle. Light beam 9 (having emerged from the front surface 2) also impinges on second element 5 at the pseudo-Brewster angle.

The incident light penetrates a filter element, where it may be partially or completely absorbed. In certain aspects, filter elements include material(s) that provide radiation absorptive properties at the desired wavelength(s) of radiation. Examples of useful materials include absorptive glass (e.g., Schott glass NG9, VG20), semiconductor materials (e.g., silicon), metals, graphite, liquid solutions of dyes, (e.g. ADS1075A—http://www.adsdyes.com/nirdyes.html) etc.

One advantage of the present embodiments is a reduction of the amount of light scattered and/or reflected from a beam blocking filter element, which improves the performance of spectral measurement instruments (e.g., in which laser or other radiation sources are used) using such filter(s).

Figure 3:
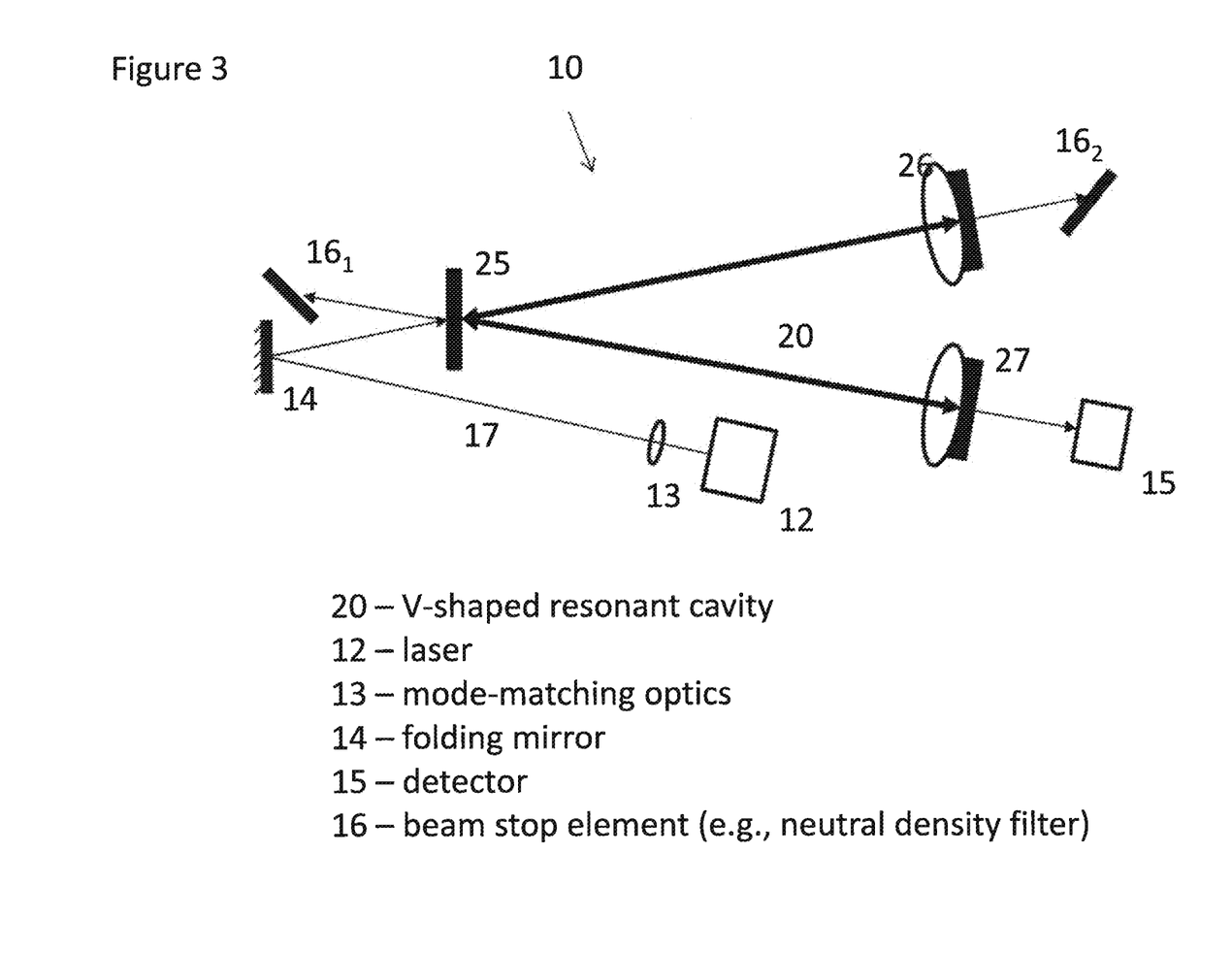
FIG. 3 shows an exemplary cavity enhanced optical spectroscopy (CEOS) system including a linear, V-shaped optical cavity configuration according to one embodiment.
Figure 4:
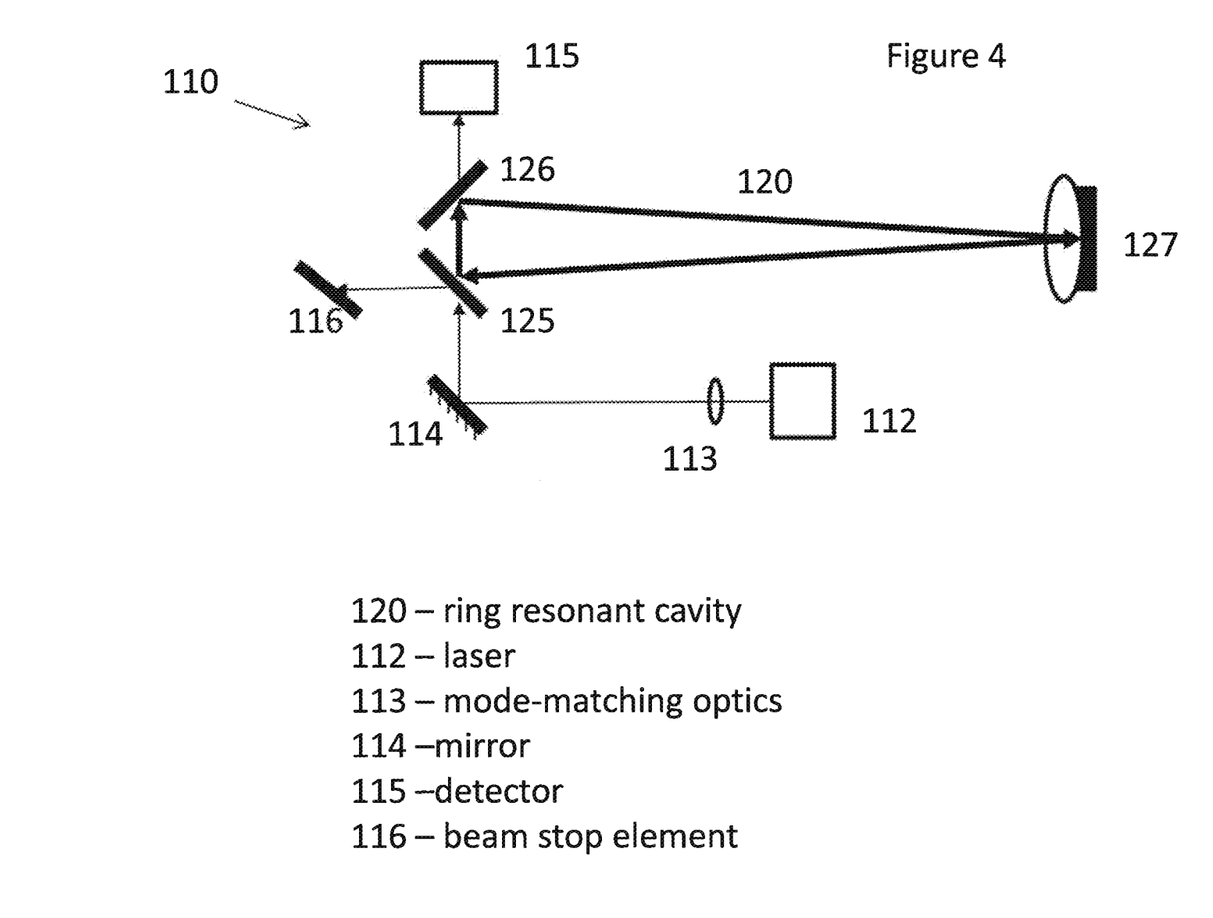
FIG. 4 shows an exemplary cavity enhanced optical spectroscopy (CEOS) system including a V-shaped, ring-resonant optical cavity configuration according to one embodiment.
Figure 5:
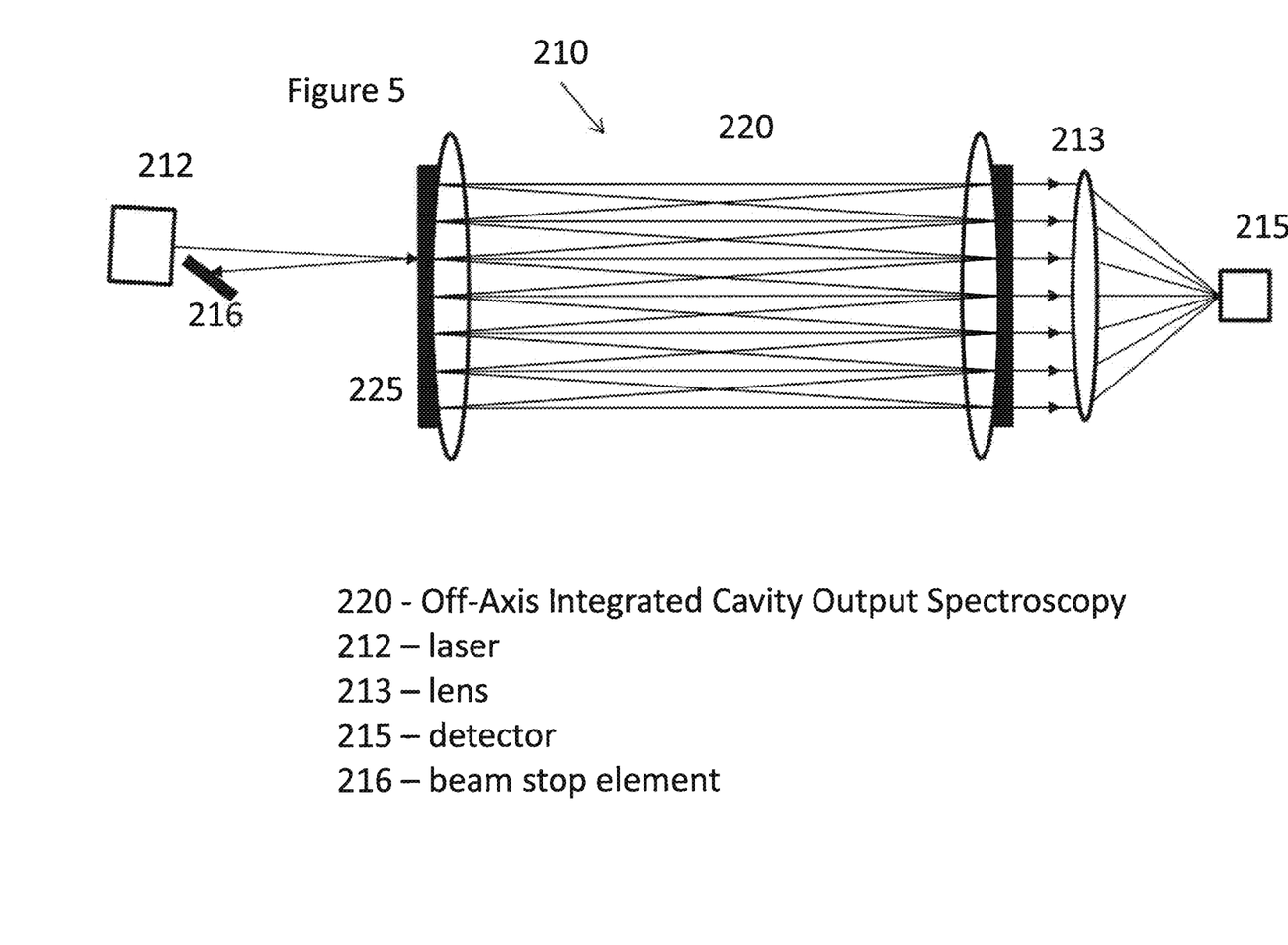
FIG. 5 shows an exemplary Off-Axis Integrated Cavity Output Spectroscopy (Off-Axis ICOS) cavity configuration according to an embodiment.

FIGS. 3-5 illustrate examples of Spectroscopy system configurations incorporating beam filtering elements according to certain embodiments. In FIG. 3, a spectroscopy instrument including a linear, V-shaped resonant optical cavity 20 and two filter elements 16 is shown. In FIG. 4, a spectroscopy instrument including a ring resonant optical cavity 120 and a filter element 116 is shown. In FIG. 5, an Off-Axis ICOS spectroscopy instrument including a resonant optical cavity 220 and a filter element 216 is shown. Although not shown herein, a cavity configuration including only two mirrors may be used, with one or more beam filtering elements as described herein positioned or located to interact with light reflecting off of a cavity mirror and/or exiting the cavity via a cavity mirror, or reflecting off of any other optical element in the system.

FIG. 3 shows an exemplary cavity enhanced optical spectroscopy (CEOS) system 10 according to one embodiment. CEOS system 10 includes a single laser, single resonant cavity configuration for measurement of trace gases in air, according to an embodiment. CEOS system 10 is particularly useful for measuring trace gases.

CEOS system 10 includes a light source 12 that emits continuous wave coherent light, such as continuous wave laser light, and an optical cavity 20. A detector system (including one or more photodetectors) is provided and configured to measure absorption within the cavity, and hence an absorption coefficient, as well as other characteristics of incident and/or reflected light. In one embodiment, the detector system includes a photodetector 15 configured and arranged to measure optical signal emerging from one of the cavity mirrors. As shown, cavity 20 is a V-shaped cavity defined by cavity coupling mirror 25 and mirrors 26 and 27. One or more optical components are configured and arranged to facilitate directing, and mode matching laser light from source 12 to the optical cavity 20 via cavity coupling mirror 25. In one embodiment, for example, mode matching optics 13 and mirror 14 are provided to mode-match and direct the laser light (beam 17) to cavity 20. Optional beam splitting elements (BS) may be included. Cavity coupling mirror 25, in one embodiment, is arranged at an angle with respect to the incident source beam. A portion of incident light from the source enters cavity 20 via mirror 25. Depending on the frequency of incident light and the optical length of cavity 20 (e.g., optical length from mirror 27 to mirror 25 to mirror 26), light circulating in the cavity 20 may build up and resonate at one or a plurality of cavity modes (cavity resonances evenly separated in frequency; commonly known as the FSR or free spectral range of the cavity). A small portion of the intracavity light circulating in cavity 20 between mirror 27, 25 and 26, emerges or escapes via mirror 27 and also mirrors 26 and 25 as determined by their transmissivity. The light escaping mirror 25 is controlled by the various mirrors and other optical elements to pass back to the source 12, e.g., for optical feedback. In certain aspects, light returning to the source may pass through optional phase control and/or attenuation elements (not shown), which advantageously provides for phase and/or intensity control of the optical feedback provided to source 12 from cavity 20. Examples of useful phase control and/or attenuation elements might include an electro-optic modulator that imposes a modulation on the phase of the light and an attenuation element such as a Faraday rotator.

An optional enclosure or housing (not shown) provides an air tight seal for components within the housing, such as cavity 20, laser sources 12 and 14 and the various optical elements such as to allow control of the environment within the housing and hence also the cavity 20. Enclosed cavities are desirable for certain applications. The optional enclosure may be made of any suitable, structurally stable material, such as a metal or metal alloy, or a plastic material.

In certain embodiments, CEOS system 10 also includes a temperature sensor positioned and configured to measure a temperature of the gas within cavity 20 and a pressure sensor positioned and configured to measure a pressure of the gas within cavity 20. It should be appreciated that more than one temperature sensor may be used, and that more than one pressure sensor may be used. For example, a single temperature sensor may be used to determine a temperature internal to the cavity, or where gas is flowed through the cavity, for example, two temperature sensors may be used to determine a temperature at a gas inflow port and a gas exhaust port, from which a temperature of the gas in the cavity can be determined. In certain embodiments, the temperature and pressure of the gas in the cavity is controlled using a temperature control element and a pressure control element. Control of the ambient conditions, e.g., temperature and/or pressure, can be useful to help improve signal resolution and SNR.

In one embodiment, CEOS system 10 includes one or more beam stop elements 16 to block unwanted beam reflections. A shown in FIG. 3, a first beam stop element 16₁ might be located and arranged (e.g., oriented at appropriate angle such as Brewster angle or pseudo-Brewster angle) to interact with light reflected by mirror 25 and/or to interact with light exiting the cavity 20 via mirror 25 so as to reduce or eliminate unwanted light reflecting or scattering within system 10. Alternately, or additionally, a second beam stop element 16₂ might be located and arranged to interact with light exiting the cavity 20 via mirror 26 so as to reduce or eliminate unwanted light reflecting or scattering within system 10. Alternately, or additionally, a beam stop element might be located and arranged elsewhere to interact with light traversing the system 10. It should be appreciated that each beam stop element 16 may comprise two (or more) beam stop elements in series, e.g., as discussed with reference to FIG. 2 and FIG. 6.

FIG. 4 shows a CEOS system 110 including a single laser, single resonant cavity configuration for measurement of trace gases in air, according to an embodiment. CEOS system 110 is similar to CEOS 10, but includes a ring resonant optical cavity configuration 120. In one embodiment, the detector system includes a photodetector 115 configured and arranged to measure optical signal emerging from one or more of the cavity mirrors. As shown, cavity 120 is a V-shaped cavity defined by cavity coupling mirror 125 and mirrors 126 and 127. One or more optical components, such as directing mirror 114 and/or lens elements 113, are configured and arranged to facilitate directing, and mode matching laser light from sources 112 to the optical cavity 120 via cavity coupling mirror 125. Optional beam splitting elements (BS) may be included. Depending on the frequency of incident light and the optical length of cavity 120 (e.g., optical length from mirror 127 to mirror 125 to mirror 126), light circulating in the cavity 120 may build up and resonate at one or a plurality of cavity modes (cavity resonances evenly separated in frequency by a free spectral range of the cavity (FSR)). A small portion of the intracavity light circulating in cavity 120 between mirror 127, 125 and 126, emerges or escapes via mirror 126 and also mirrors 127 and 125 as determined by their transmissivity. The light escaping mirror 125 is controlled by the various mirrors and other optical elements to pass back to the source 112, e.g., for optical feedback. In certain aspects, light returning to sources may pass through optional phase control and/or attenuation elements, which advantageously provides for phase and/or intensity control of the optical feedback provided to source 112 from cavity 120. Examples of useful phase control and/or attenuation elements might include an electro-optic modulator that imposes a modulation on the phase of the light and an attenuation element such as a Faraday rotator.

An optional enclosure or housing (not shown) provides an air tight seal for components within the housing, such as cavity 120, laser source 112 and the various optical elements such as to allow control of the environment within the housing and hence also the cavity 120. Enclosed cavities are desirable for certain applications.

In certain embodiments, system 110 also includes one or more temperature sensors positioned and configured to measure a temperature of the gas within cavity 120 and one or more pressure sensors positioned and configured to measure a pressure of the gas within cavity 120 as discussed above for FIG. 1. CEOS system 110 may also include temperature and/or pressure control elements as discussed above for FIG. 1.

In one embodiment, CEOS system 110 includes one or more beam stop elements 116 to block unwanted beam reflections. As shown in FIG. 4, a beam stop element 116 might be located and arranged (e.g., oriented at appropriate angle such as Brewster angle or pseudo-Brewster angle) to interact with light reflected by mirror 125 and/or to interact with light exiting the cavity 20 via mirror 125 so as to reduce or eliminate unwanted light reflecting or scattering within system 110. Alternately, or additionally, a beam stop element might be located and arranged elsewhere to interact with light traversing the system 110. An example might be a beam stop element located to interact with light exiting the cavity 20 via mirror 127 so as to reduce or eliminate unwanted light reflecting or scattering within system 10. It should be appreciated that each beam stop element 116 may comprise two (or more) beam stop elements in series, e.g., as discussed with reference to FIG. 2 and FIG. 6.

FIG. 5 shows an Off-Axis Integrated Cavity Output Spectroscopy (ICOS) Cavity configuration according to an embodiment. The ICOS method allows narrowband continuous-wave lasers to be used in conjunction with optical cavities. The absorption signal is obtained through the integration of the total signal transmitted through the optical cavity [http://www.lgrinc.com/publications/spie2.pdf , Joshua B. Paul; James J. Scherer; Anthony O'Keefe; Larry Lapson; Janelle R. Anderson; Claire F. Gmachl; Federico Capasso; Alfred Y. Cho, Proc. SPIE 4577, Vibrational Spectroscopy-based Sensor Systems, 1 (Feb. 13, 2002); http://proceedings.spiedigitallibrary.org/proceeding.aspx?articleid=901633]. Light impinging on cavity coupling mirror 225 enters the cavity 220 in a manner such that the light reflects back and forth between the mirrors defining cavity 220. In one embodiment, the detector system includes a photodetector 215 configured and arranged to measure an optical signal emerging from the distal cavity mirror. One or more optical components, such as lens element 213, is configured and arranged to facilitate directing and focusing radiation emerging from the distal mirror of cavity 220 onto the detector 215.

In one embodiment, CEOS system 210 includes one or more beam stop elements 216 to block unwanted beam reflections. As shown in FIG. 5, a beam stop element 216 might be located and arranged (e.g., oriented at appropriate angle such as Brewster angle or pseudo-Brewster angle) to interact with light reflected by mirror 225 and/or to interact with light exiting the cavity 220 via mirror 225 so as to reduce or eliminate unwanted light reflecting or scattering within system 210. Alternately, or additionally, a beam stop element might be located and arranged elsewhere to interact with light traversing the system 210. It should be appreciated that each beam stop element 216 may comprise two (or more) beam stop elements in series, e.g., as discussed with reference to FIG. 2 and FIG. 6.

Figure 6:
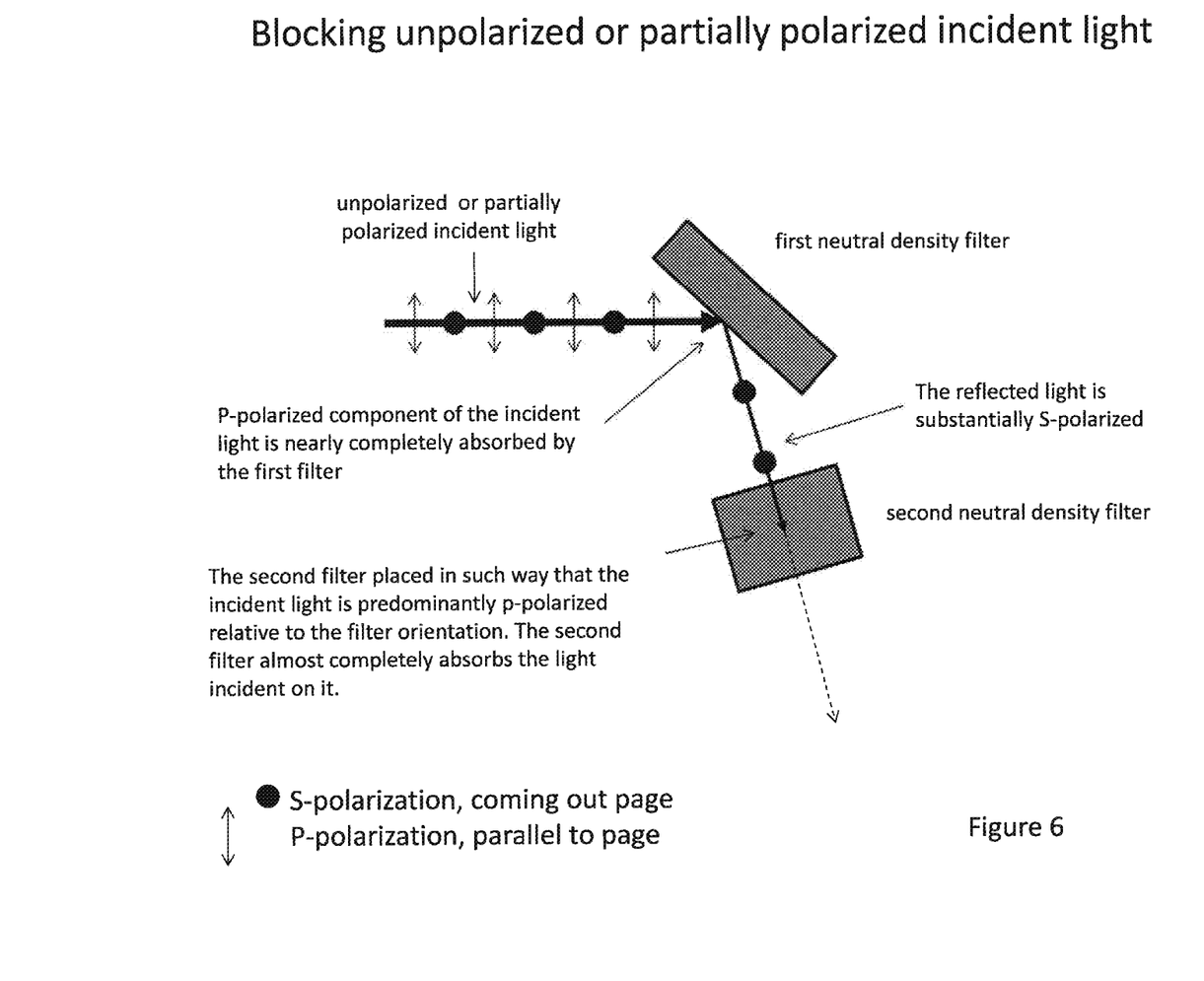
FIG. 6 illustrates the capability of two filter elements of the present embodiments to block polarized and un-polarized incident light.

FIG. 6 illustrates the capability of two filter elements of the present embodiments to block polarized and un-polarized incident light. It should be appreciated that any two filter elements may operate as a variable neutral density filter to control the amount of light filtered, e.g., polarizing filter elements may be rotated or adjusted to control the amount of light filtered or reflected.

In certain aspects, each source (e.g., source 112 or 12 or 212) includes a laser or other coherent light source that may be sensitive or responsive to optical feedback and that emits radiation at the desired wavelength(s) or desired wavelength range(s). One useful laser is a semiconductor diode laser that is sensitive to optical feedback from light impinging on the laser from the cavity coupling mirror (e.g., mirror 25 or 125 or 225). Other laser sources might include diode lasers, quantum cascade lasers and solid state lasers. Each beam of light emitted by a source might be linearly polarized, elliptically polarized or unpolarized. Similarly, depending on interactions with various optical components of the system, reflected or scattered light might have a different polarization than the beam emitted by the source and may be linearly polarized, elliptically polarized or unpolarized.

The reflectivities of the mirrors defining the cavity define the optical feedback intensity. U.S. Pat. No. 8,659,758, which is incorporated herein by reference in its entirety, discloses laser based cavity enhanced spectroscopy systems including mirror optimization techniques. It should be appreciated that the cavity coupling mirror (e.g., mirror 25, 125, 225) through which the laser light enters the cavity has a power reflectivity coefficient $R_1$ close to, but less than, unity such that the quantity $T=1-R_1$ is in the range from $10^{-1}$ to $10^{-5}$. The other cavity mirror(s) should have a power reflectivity $R_2$ equal to or lower than $R_1$. Such high reflective mirrors will certainly have some residual transmission, even though it may be as low as a few or several ppm.

In certain aspects, each source is capable of being frequency scanned, for example, a mean optical frequency of the laser is adjustable or tunable over a range of frequencies. This can be accomplished as is well known, such as, for example, by adjusting the current applied to a diode laser and/or adjusting a temperature of the laser medium. In certain aspects, the cavity (e.g., cavity 20 or 120 or 220) is also capable of being frequency scanned, e.g., by changing or adjusting an optical length of the cavity, whereby an optical frequency of a cavity resonance peak is adjustable over a range of frequencies. Adjustment of the optical length of the cavity can include adjusting a relative position of one or more of the cavity mirrors (e.g., using a piezo element), and/or adjusting a pressure of the medium within the cavity. An intelligence module or control module, such as a computer system, processor, ASIC or other control circuitry, is provided to enable automated control of the source frequency tuning or scanning and/or cavity optical length adjustment.

In certain embodiments, the CEOS system (e.g., system 10 or 110 or 210) is useful for detecting trace gases within a gas mixture present in the cavity. When the frequency of the incident light emitted by a source approaches the frequency of one of the cavity modes, the incident light entering the cavity begins to fill the cavity to that mode and may lock to that cavity mode. The optical intensity of the light circulating inside the resonance cavity reflects total cavity loss at the moment when the light frequency of incident light coincides with the cavity mode transmission peak. The total cavity loss is a sum of the cavity mirror losses and losses caused by absorption by the medium present in the cavity, e.g., absorption caused by absorbing analyte species present in the gaseous or liquid medium in the cavity. Examples of such species detectable by embodiments herein include $H_2O$, $N_2O$, NO, $NO_2$, $CO_2$, $CH_4$, various hydrogen, carbon, nitrogen and oxygen isotopes, and many others.

In various embodiments, the detector system is configured take measurements from which an absorption coefficient can be determined, e.g., based on measuring the intracavity optical power with and without an absorbing species present. For example, the power circulating inside the cavity ($P_{circ}$) is determined by the equation $P_{transm}=P_{circ}*T$, where T is the transmissivity of the mirror from which the light is escaping, and $P_{transm}$ is the power detected by the detector. A detector or detection element may be proximal to mirror element (e.g., 27 or 127 or 227, or other mirror). It should be appreciated that a detection element can additionally, or alternatively, be positioned to detect and measure the light escaping from mirror element 26 or 126 or 226 and/or mirror element 25 or 125 or 225. Also, a detection element could be configured and positioned internal to the cavity to measure the intracavity optical power. In certain embodiments, each detector element includes a photodetector, such as a photodiode, and associated electronics, for detecting light and outputting a signal representing the detected light. Examples of useful photodetectors might include silicon, InGaAs, Ge or GAP based photodetectors. Other useful detectors include CCDs, photomultipliers, etc. An intelligence module (e.g., a computer system, processor, ASIC or other control circuitry; not shown) receives the detector output signals and processes these signals to produce or generate a signal that characterizes the cavity loss based on the detection methodology used, e.g., PAS, free decay rate, phase shift, direct absorption, etc. For example, U.S. Pat. No. 8,659,759, which is incorporated herein by reference in its entirety, discloses laser based cavity enhanced spectroscopy systems including techniques for producing normalized signals that are a linear function of total cavity loss and that are not sensitive to laser-cavity coupling.

Additionally, as mentioned above, other detection methods can be used, for example, cavity ring-down spectroscopy methods, or cavity enhanced photo-acoustic spectroscopy (PAS) methods (see, e.g., U.S. Pat. No. 8,327,686, the contents of which are hereby incorporated by reference). Measurements made by the detector system are used to determine an absorption coefficient for any gas species or isotopes present in the cavity. For CRDS measurements, the ring-down decay time is measured and used to determine the absorption coefficient.

Reference is also made to U.S. Pat. Nos. 8,659,758, 8,659,759, 8,885,167 and 8,665,442 which are each hereby incorporated by reference for all purposes, for laser spectroscopy based gas analyzer systems and applications for which the present embodiments are useful.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A laser-based spectroscopy system, the system comprising:
   a laser source that emits a beam of radiation;
   an optical resonant cavity having at least two cavity mirrors; and
   at least one beam filtering element positioned along a path of the beam external to the cavity and having a front surface, wherein the front surface is oriented such that an intersection of the beam and the surface is at an angle that reduces or eliminates reflection of a predominant polarization component of the beam by the filtering element.

2. The system of claim 1, wherein the laser source is a diode laser source.

3. The system of claim 1, wherein the at least one beam filtering element comprises an absorptive glass material.

4. The system of claim 3, wherein the angle is at a pseudo-Brewster angle.

5. The system of claim 1, wherein the angle is at a Brewster angle.

6. The system of claim 1, comprising at least two beam filtering elements, each positioned along a path of the beam and having a front surface, wherein each said front surface is oriented such that an intersection of the beam and said front surface is at an angle that reduces reflection of a predominant polarization component of the beam by said surface.

7. The system of claim 1, wherein the at least one beam filtering element is positioned to receive light reflected off of one of said cavity mirrors.

8. The system of claim 1, wherein the at least one beam filtering element is positioned to receive light emerging from one of said cavity mirrors.

9. The system of claim 1, wherein the at least one beam filtering element comprises a neutral density filter.

10. The system of claim 1, further comprising a second beam filtering element positioned to interact with light reflected from the at least one beam filtering element.

11. An apparatus for detecting one or more analyte species present in a gaseous or liquid medium, the apparatus comprising:
   a resonant optical cavity having at least two cavity mirrors, one of which is a cavity coupling mirror;
   a laser that emits a beam of laser light;

mode matching optics configured to couple the beam of laser light to the cavity via the cavity coupling mirror;

a detector configured to measure an intensity of intracavity optical power of light circulating in the cavity and to generate a signal representing the intracavity optical power of light circulating in the cavity; and a first beam stop element positioned external to the resonant optical cavity and arranged such that an intersection of the beam and a front surface of the first beam stop element is at an angle that reduces or eliminates reflection of a predominant polarization component of the beam by the first beam stop element.

12. The apparatus of claim 11, wherein the laser is a diode laser.

13. The apparatus of claim 11, wherein the first beam stop element comprises an absorptive glass material, and wherein the angle is at a pseudo-Brewster angle.

14. The apparatus of claim 11, wherein the angle is at a Brewster angle.

15. The apparatus of claim 11, wherein the first beam stop element is positioned to receive light reflected off of one of said at least two cavity mirrors.

16. The apparatus of claim 11, wherein the first beam stop element is positioned to receive light emerging from one of said at least two cavity mirrors.

17. The apparatus of claim 11, wherein the first beam stop element comprises a neutral density filter.

18. The apparatus of claim 11, further comprising a second beam stop element positioned to interact with light reflected from the first beam stop element.

* * * * *